United States Patent [19]
Suda et al.

[11] Patent Number: 5,869,235
[45] Date of Patent: Feb. 9, 1999

[54] GENE OF THE HOP LATENT VIRUS AND METHODS FOR DETECTING THE SAME

[75] Inventors: Narushi Suda; Yutaka Itoga, both of Sorachi; Tatsuzi Hataya, Sapporo, all of Japan

[73] Assignee: Sapporo Breweries Ltd., Tokyo, Japan

[21] Appl. No.: 736,723

[22] Filed: Oct. 25, 1996

[30] Foreign Application Priority Data

Oct. 27, 1995 [JP] Japan .................................. 7-302297
Dec. 28, 1995 [JP] Japan .................................. 7-352285

[51] Int. Cl.⁶ .............................. C12Q 1/70; C12Q 1/68; C12P 19/34; C07H 21/04
[52] U.S. Cl. ................................. 435/5; 435/6; 435/91.2; 536/23.72; 536/24.32; 935/8; 935/17; 935/77; 935/78
[58] Field of Search ............................. 435/4, 5, 6, 91.2, 435/91.51; 536/23.1, 23.72, 24.32; 935/6, 8, 17, 77, 78

[56] References Cited

FOREIGN PATENT DOCUMENTS 6-303999  1/1994  Japan .

OTHER PUBLICATIONS

Foster et al. Virus Genes 5:327–334, Oct. 1991.
Hataya et al. Ann. Phytopath. Soc. Japan 58:677–684, 1992.
Langeveld et al. J. Gen. Virol. 72:1531–1541 (Jul. 1991).
"Host Range, General Properties, Purification, and Electron Microscopy of Hop Latent Virus," E. G. Probasco et al. Phytopathology (1978) vol. 68; pp. 277–281.
"Host Range, Purification and Some Properties of Two Carlaviruses From Hop (Humulus Lupulus): Hop Latent and American Hop Latent," A. N. Adams et al. Ann. Appl. Biol. (1982), 101; pp. 483–495.

Masayasu Inoue, "Nature and Pathogenicity of Rahbdoviruses Separated from Hops", Japan Plant Pathology Society Report, vol. 39, No. 3, Jun. 1973 with English Translation.

Andrea Gramstat et al., "The 12 kDa Protein of Potato Virus M Displays Properties of a Nucleic Acid–Binding Regulatory Protein", Febs. Letters, vol. 276, No. 1, 2, Dec. 10, 1990.

Y. Kanno et al., "Some Properties of Hop Latent and Apple Mosaic Viruses Isolated from Hop Plants and Their Distributions in Japan", Database Biosis, Biosciences Information Service, Philadelphia, PA, DN 9719602, Ann. Phytopath. Soc. Jap., 59, 651–58, 1993, Abstract.

Database WPI, Section Ch, Week 9232, Derwent Publications Ltd., London, GB, Class G01, AN 92–264502, XP002061747 & JP 04 181 162 A (Nippon Mining Co.), Jun. 29, 1992, Abstract.

Database WPI, Section Ch, Week 9503, Derwent Publications Ltd., London GB; Class C12, AN 95–018290, XP002061748 & JP 06 304 000 A (Sumitomo Chemicals Co Ltd), Nov. 1, 1994, Abstract.

Database WPI, Section Ch, Week 9503, Derwent Publications Ltd., London, GB; Class C12, AN 95–018289, XP00206749 & JP 06 303 999 A (Sumitomo Chemicals Co Ltd), Nov. 1, 1994 Abstract.

*Primary Examiner*—W. Gary Jones
*Assistant Examiner*—Debra Shoemaker
*Attorney, Agent, or Firm*—Oblon, Spivak, McClelland, Maier & Neustadt, P.C.

[57] ABSTRACT

DNA, a gene derived from the genome of the hop latent virus, encoding the coat protein of the virus and having the base sequence described in the sequence identification number 1 in the sequence listing. The DNA is useful of a development of an efficient gene diagnostic method for detecting the hop latent virus-infected plant.

15 Claims, 2 Drawing Sheets

```
                                                        170
                                              AAGATGAGTT GCTTAAG
     180
AAG TAC ATT GAT CCT GGG CTA GGG TCT GAT GAT GAT GAA GAG GAG ATG GTG
Lys Tyr Ile Asp Pro Gly Leu Gly Ser Asp Asp Asp Glu Glu Gln Met Val

240
GAATTGAGATTG AGCAAATTGA GGGAGTTCCT GGCTCGTAGA AGGGCCGCTA TTCGCGTGAC
                                        330
TAACGCAGGG CTAGAAACAG GCAGGCCCGC ACTCAAGCCC ACACCCGAC ATG CTG CCT
                                                           Met Leu Pro

380
GAC CCT ACC AAC CCG TAC AAT AAACCCTCGTT GGATGCTTTG TTGATGATTA AGCCTA
Asp Pro Thr Asn Pro Tyr Asn

450
GGGT CGTGTCAAAC AACATGGCCA CCTCAGAGGA TATGATGAAG ATC TGC GTT GAT
                                                     Ile Cys Val Asp

490
CTG GAG GGG TTG GGC GTG CCC ACTGAAC ACGTGCAAAG CGTGATCTTG CAAGCGGTGT
Leu Glu Gly Leu Gly Val Pro
```

GENE OF THE HOP LATENT VIRUS AND METHODS FOR DETECTING THE SAME

BACKGROUND OF THE INVENTION

1. Field of the Invention

The present invention relates to genes of the hop latent virus and methods for detecting said virus.

2. Description of the Related Arts

Infection with the hop latent virus (abbreviated as HLV hereafter) has been reported to widely spread in all hop cultivation areas (Tresh & Ormerod, Rep. E. Malling Res. Stn. for 1968: 41 (1969); Probasco & Skotland, Phytopathology 68: 278 (1978); Adams & Barbara, Ann. appl. Biol., 101: 483 (1982); Inoue et al., Ann. Phytopath. Soc. Japan 39: 229 (1973)).

This HLV is in filamentous shape belonging to the carlavirus group. Neither the gene structure nor the primary structure of the coat protein thereof have been elucidated. Therefore, enzyme linked immuno sorbent assay (ELISA) is employed using the antibody of HLV as the method for selecting virus-free clones of the hop. However, the diagnostic detection of HLV by ELISA has posed various problems such as the reduction in the detection sensitivity depending on the harvest time of samples and the tedious preparation of antibodies.

In view of the above mentioned circumstances, the present invention aims to solve these problems by developing efficient and accurate methods for detecting HLV-infected plants.

SUMMARY OF THE INVENTION

By analyzing and examining the HLV gene, the present inventors were the first who succeeded in identifying the gene of HLV coat protein and elucidating the base sequence thereof as well as the primary structure of said protein.

With genetic procedure utilizing the gene of HLV coat protein or DNA synthesized according to the base sequence thereof, HLV can be detected by genetic procedures such as polymerase chain reaction (abbreviated as PCR hereafter) and Southern hybridization. For example, in the PCR with portions of the base sequence or DNA comprising the complementary sequence thereof as a primer, HLV is detected through the production of amplified DNA products specific to the HLV-infected plant. In addition, in hybridization using the complementary DNA strand of the HLV gene as a probe, positive specific bands may be observed with HLV-infected plants by Southern blot analysis.

A first aspect of the present invention features DNA encoding the coat protein of the hop latent virus comprising a base sequence described in the sequence identification number 1 in the sequence listing, wherein, of the base sequence described in the sequence identification number 1 in the sequence listing described above, a) the base sequence from 58th to 975th encodes 306 amino acid residues; and b) the base sequence from 981st to 1292nd encodes 104 amino acid residues.

The gene, including DNA and RNA, encoding HLV coat protein and portions thereof can be used for the genetic method for detecting the HLV. As probes utilized for PCR and Southern hybridization, the following base sequences from the sequence listing may be preferably used, for example, a) sequence identification number 2 (corresponding to from 405th to 423rd in the sequence identification number 1), b) sequence identification number 3 (corresponding to from 457th to 474th in the sequence identification number 1), c) sequence identification number 4 (corresponding to from 618th to 637th in the sequence identification number 1), and d) sequence identification number 5 (corresponding to from 761st to 781st in the sequence identification number 1).

These DNAs may be obtained from the RNA extracted and purified from the HLV, and also prepared using an automated DNA synthesizer. Especially, short single-stranded DNAs such as base sequence identification numbers from 2 to 5 may be obtained conveniently by chemical synthesis.

Another aspect of the present invention features a method for detecting the HLV, wherein the method comprises amplification of DNA by the reverse transcription PCR performed with nucleic acid extracted from the hop serving as a template and any one of synthetic DNAs of sequence identification numbers from 2 to 5 serving as a primer, and electrophoretic analysis of amplified products thus obtained.

More specifically, the HLV can be detected by DNA amplification by reverse transcription PCR with synthetic DNAs of sequence identification numbers 2 and 4 serving as primers followed by electrophoretic analysis of amplified products thus obtained confirming the presence of a specific DNA fragment comprising 233 base pairs.

Similarly, the HLV can be detected by DNA amplification by reverse transcription PCR with synthetic DNAs of sequence identification numbers 3 and 4 serving as primers followed by electrophoretic analysis of amplified products thus obtained confirming the presence of a specific DNA fragment comprising 181 base pairs.

Also, the HLV can be detected by DNA amplification by reverse transcription PCR with synthetic DNAs of sequence identification numbers 2 and 5 serving as primers followed by electrophoretic analysis of amplified products thus obtained confirming the presence of a specific DNA fragment comprising 377 base pairs.

Furthermore, the HLV can be detected by DNA amplification by reverse transcription PCR with synthetic DNAs of sequence identification numbers 3 and 5 serving as primers followed by electrophoretic analysis of amplified products thus obtained confirming the presence of a specific DNA fragment comprising 325 base pairs.

A third aspect of the present invention features a method for detecting HLV, wherein the method comprises hybridization of nucleic acid extracted from hop and primer comprising synthetic DNA of either sequence identification numbers 4 or 5, or complementary strand DNA elongated with the DNAs serving as a primer.

A fourth aspect of the present invention features a method for detecting HLV, wherein the method comprises nucleic acid extracted from hop and restriction enzyme fragment of DNA described in sequence identification number 1 serving as a probe.

A fifth aspect of the present invention features a HLV coat protein translated from the base sequence from 58th to 975th of the sequence identification number 1 in the sequence listing comprising 306 amino acid residues of the sequence identification number 6 in the sequence listing.

DESCRIPTION OF THE PREFERRED EMBODIMENT

In the present invention, the gene of HLV is analyzed by the following procedures to identify that of HLV coat protein and elucidate the base sequence thereof.

1. Isolation of HLV

HLV may be isolated from the hop by standard methods, for example, comprising concentration of the virus with polyethylene glycol, clarification of the extract by organic solvents and heat treatment, fractional centrifugation, sucrose density gradient centrifugation, etc.

2. Extraction of RNA from HLV

The extraction can be performed by standard methods such as SDS-phenol method mainly used for other plant viruses.

3. Cloning of cDNA

Utilizing RNA extracted from HLV particles as a template, a double-stranded cDNA is synthesized in vitro according to Gubler-Hoffman's method (Gubler & Hoffman, Gene, 25, 263 (1983)). cDNA thus synthesized is incorporated into a plasmid vector by ligation using standard techniques. Plasmid vectors to be used are exemplified by pUC119, pBluesriptII, etc. Competent E. coli cells are transformed using said ligation mixture. From the transformant thus obtained, recombinant plasmid cloning cDNAs are selected and purified.

4. Determination of base sequence of cDNA derived from the HLV genome using recombinant plasmid obtained by the method described above, the base sequence can be determined according to Maxam-Gilbert's method (Maxam & Gilbert, Proc. Natl. Acad. Sci., 74, 560 (1977) or the dideoxy method (Sanger et al., Proc. Natl. Acad. Sci., 74, 5463 (1977)).

Thus, the base sequence of DNA comprising the gene encoding the HLV coat protein (abbreviated as HLV coat protein gene hereafter) is determined, and described in the sequence identification number 1 in the sequence listing.

5. Determination of partial amino acid sequence of the HLV coat protein

Figure 1:
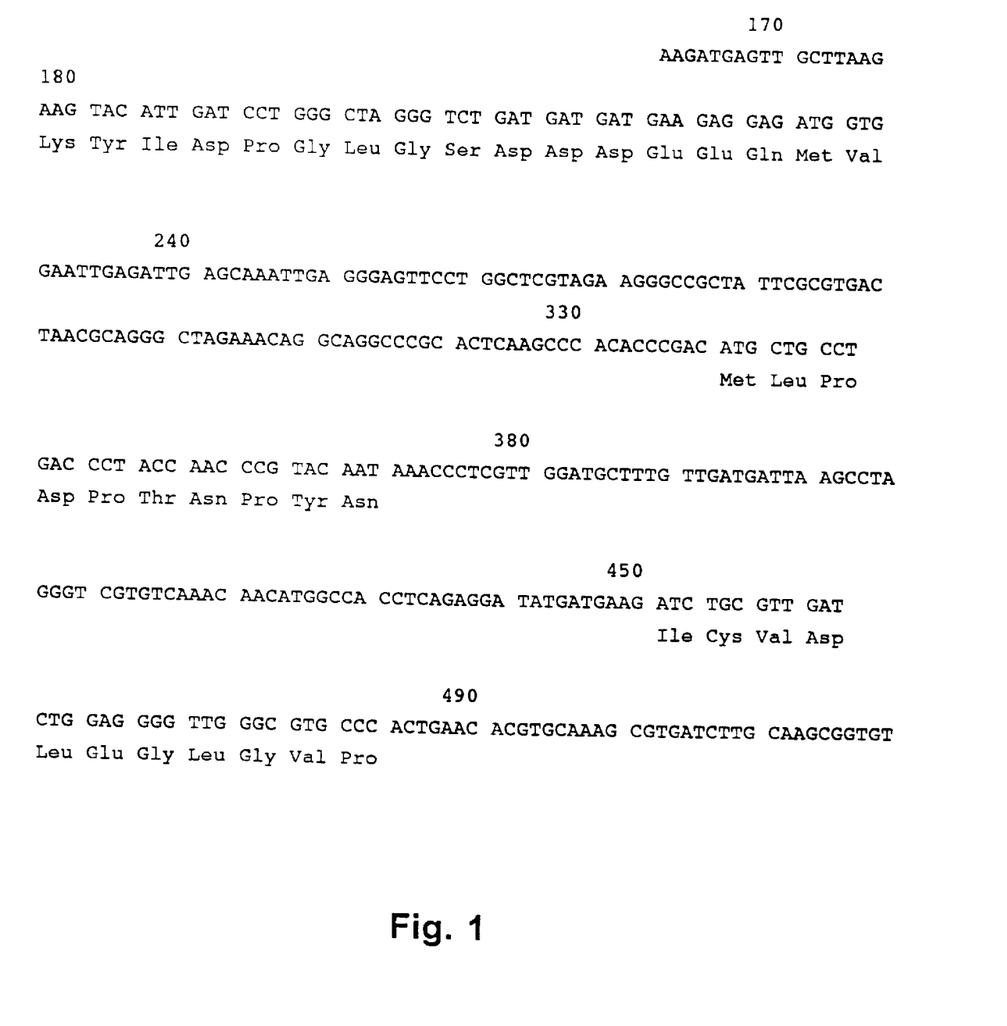
FIG. 1 shows the amino acid sequence of the coat protein of hop latent virus analyzed by a protein sequence analyzer (bases 161–520 of SEQ ID NO:1 and residues 41–57, 95–104 and 132–142 of SEQ ID NO:6).

This is carried out using a protein sequencer (ABI) after a partial digestion of the HLV coat protein followed by fractionation and purification of the digests by high-performance liquid chromatography. A partial amino acid sequence of the HLV coat protein thus determined is shown in FIG. 1. By comparing this partial amino acid sequence with that of the HLV coat protein deduced from the base sequence of the HLV coat protein gene shown in the sequence listing, the primary structure (amino acid sequence) of the coat protein has been elucidated (see FIG. 1).

6. Viral gene diagnosis of the HLV-infected hop

1) Gene diagnosis by reverse transcription PCR

A primer DNA of about 20 bases long comprising the partial base sequence of HLV coat protein gene determined by the method described above or that of complementary strand of the base sequence is synthesized by standard methods. Viral gene diagnosis of the HLV-infected hop becomes possible by detecting the presence or absence of amplified products obtained by PCR using said primer.

Oligonucleotides comprising the base sequence of sequence identification numbers from 2 to 5 in the sequence listing may be used as primers. Among them, the base sequence described in sequence identification number 2 in the sequence listing is the same as that from 405th to 423rd of the base sequence described in sequence identification number 1, and designated 3P hereafter. The base sequence described in the sequence identification number 3 in the sequence listing is the same as that from 457th to 474th of the base sequence described in the sequence identification number 1, and designated 4P hereafter. Also, the base sequence described in the sequence identification number 4 in the sequence listing is the complementary strand of the base sequence from 618th to 637th of the base sequence described in the sequence identification number 1, and designated 3M hereafter. The base sequence described in the sequence identification number 5 in the sequence listing is the complementary strand of the base sequence from 761st to 781st of the base sequence described in the sequence identification number 1, and designated 4M hereafter.

Also, synthetic oligonucleotides comprising a portion of base sequences described in the sequence identification numbers from 2 to 5 may be used as primers. That is, since PCR is primarily a method for amplifying copy of specific gene information obtained out of many base sequences, oligonucleotides comprising the base sequence similar to that of the primer of the present invention may be used similarly to primers.

Primer DNA used in the present invention can be obtained by, for example, a β-cyanoethylphosphoamidite method or a commercial automated DNA synthesizer using the thiophosphite method.

Nucleic acid from the hop plant used in the present invention can be extracted by any standard method, such as the conventional nucleic acid extraction method.

Using the nucleic acids of the hop thus obtained and primers described above, DNAs derived from the HLV genome are amplified by techniques which combine the reverse transcription of the viral RNAs with the polymerase chain reaction (PCR). PCR is a procedure of the repetitive DNA replication cycle comprising steps of denaturation, primer annealing and elongation by DNA polymerase, and the general method thereof is described, for example, in Saiki et al., Science, 230, 1350–1354, etc.

PCR performed in the present invention is exemplified by the method, wherein the DNA replication cycle is repeated about 20~50 times, preferably about 25~40 times in the amplification buffer consisting of 1.0 mM~4.0 mM, preferably 1.5 mM~3.0 mM $MgCl_2$ solution, which is previously mixed with synthetic oligonucleotides, DNA polymerase, 4 kinds of nucleotide (dATP, dTTP, dCTP and dGTP) and the hop DNAs, potassium chloride, gelatin, bovine serum albumin, surface active agent (Tween 20, NP-40, Triton X-100, etc. (all in trade names)), dimethylsulfoxide, etc.

Furthermore, each step in the PCR may be performed under such conditions as follows.

The denaturation step is performed by heating generally at from 90° C. to 95° C., preferably at from about 94° C. to 95° C. for about 1 min to about 3 min, preferably for about 1 min to 2 min.

The primer annealing step is carried out by incubating with primers generally at from 30° C. to 50° C., preferably at from about 35° C. to about 42° C. for from about 1 min to about 3 min, preferably for from about 1 min to about 2 min.

The elongation step with DNA polymerase is carried out by treatment with the thermostable DNA polymerase generally at from about 70° C. to about 73° C., preferably at from about 72° C. to about 73° C., for from about 1 min to about 4 min, preferably for from about 2 min to about 3 min. The thermostable DNA polymerase to be used is exemplified by the commercial products such as that from Perkin Elmer, Inc.

DNAs thus amplified can be visually detected by the staining method using compounds which can interact with nucleic acids, for example, dyes of phenanthridine series such as ethidium bromide, etc. In the staining method, when the dye, such as ethidium bromide, etc. is previously added to the electrophoresis buffer, for example, at a final concentration of about 5 $\mu$g/ml, red bands of the DNA-ethidium bromide complex can be observed even during electrophoresis by irradiating gels with ultraviolet light at 254 nm or 366 nm in the dark. However, in general, the red bands of the DNA-ethidium bromide complex are detected by immersing electrophoretic gels in a solution of ethidium bromide, etc. for about 10 to 60 min after the termination of electrophoresis followed by irradiating the gels with ultraviolet light at 254 nm or 366 nm in the dark.

Viral infection can be identified by confirming the presence or absence of amplified DNAs. That is, when the PCR is carried out using the same primer, the specific amplified DNA is detected with samples derived from the virus-infected hop, but not with samples from the uninfected hop.

For example, HLV can be detected by the presence of the specific DNA fragment comprising a) 233 base pairs in the amplification of DNA by RT-PCR using SEQ ID NOS 2 and 4 as primers, b) 181 base pairs in the amplification of DNA by RT-PCR using SEQ ID NOS 3 and 4 as primers, c) 377 base pairs in the amplification of DNA by RT-PCR using SEQ ID NOS 2 and 5 as primers, and d) 325 base pairs in the amplification of DNA by RT-PCR using SEQ ID NOS 3 and 5 as primers, respectively.

2) Gene diagnosis by hybridization

A HLV diagnosis different from the conventional immunoassay can be performed by preparing oligonucleotides having the sequence complementary to the gene encoding the HLV coat protein by either chemical synthesis or gene manipulation, and hybridizing with the nucleotide as primers.

Probes to be used are generally 20 to several thousands bases long, exemplified by, for example, those having the base sequences described in the sequence identification numbers 6 and 7 in the sequence listing, and DNA fragments produced by the restriction enzyme digestion of cDNAs prepared from plasmid obtained by cloning the HLV coat protein gene. These probes are used for the hybridization after being labeled with isotope, biotin, fluorescer, etc. by standard methods.

The hop plant nucleic acids to be used for the hybridization can be extracted by standard methods, for example, the standard nucleic acid extraction methods described, for example, in Murray & Thompson, Nucl. Acid Res., 8, 4321–4325 (1080), etc. The nucleic acids thus obtained are subjected to the denaturation treatment, and then dropped on a membrane filter, such as nitrocellulose filter or nylon filter, preferably, for example, Hybond-N$^+$ (Amersham).

The denaturation treatment of the nucleic acid are carried out by heating the nucleic acid in a solution containing formamide, formaldehyde, MOPS, acetic acid, EDTA, etc. at from 60° C. to 70° C., preferably at 65° C., for from 5 min to 20 min, preferably for 15 min followed by quick cooling. After this denaturation treatment, nucleic acid is mixed with 20×SSC, and then dropped on a membrane filter.

Hybridization is performed using the membrane filter (with the hop nucleic acid dropped) thus obtained and the probes in a hybridization solution at from 42° C. to 65° C., preferably at 46° C., for from 12 h to 20 h, preferably for 16 h. Then, the membrane filter is rinsed, dried and inspected for the presence or absence of the signal of drops with detection methods such as autoradiography, etc.

That is, a signal is detected with nucleic acids derived from the virus-infected hop because of the hybridization with a probe, but not detected with those derived from uninfected hop because of lack of hybridization.

In the following, the present invention will be described in detail with reference to examples, which are designed to illustrate, not limit, the invention.

EXAMPLE 1

Isolation of HLV

Young vine of the HLV-infected hop (1 kg) were ground in 3 volumes of 0.05M phosphate buffer (containing 0.2% ascorbic acid, 0.2% nicotine, and 0.2% PVP at pH 8.0), left to stand at room temperature for 1 hr and filtered through gauze to obtain the crude juice. The juice was heat-treated (at 55° C. for 8 min), immediately cooled in an ice-water bath, and centrifuged at 3,000×g for 30 min to obtain the supernatant. To this supernatant were added polyethylene glycol and sodium chloride at the concentration of 5% and 0.15M, respectively, and the resulting solution was stirred for 1 hr and then centrifuged at 3,000×g for 30 min. Precipitates thus obtained were suspended in 0.05M phosphate buffer (containing 0.02M EDTA at pH 7.4).

Furthermore, the above suspension was centrifuged at high-speed (at 15,000×g for 10 min) to obtain the supernatant, which was then ultracentrifuged (at 100,000×g for 120 min) to recover the precipitates. This process was repeated twice to isolate the viral fraction free from contaminants.

The precipitates thus obtained were suspended in 2 ml of 0.01M phosphate buffer (pH 8.0) and subjected to sucrose density gradient (20~10%) centrifugation (at 150,000×g for 120 min) to collect the virus-containing fraction. Finally, the fraction was centrifuged at 180,000×g for 150 min to obtain the viral particles as precipitate, which was resuspended in 0.01M phosphate buffer (pH 8.0) and stored as the purified viral preparation.

Unless stated otherwise, the procedures described above were performed under conditions at 4° C.

EXAMPLE 2

Extraction of RNA from HLV

Extraction of RNA from HLV particles were performed by the SDS-phenol method (Proll et al., Pota to Research 24, 1–10 (1981).

To the purified HLV preparation (1 $\mu$g/ml, 84 $\mu$l) obtained by the same method as in Example 1 were added 20% SDS (5 $\mu$l), 20×SCC (1 $\mu$l) and the protease (Trade name: Protease K) (10 mg/ml, 10 $\mu$l), and the resulting mixture was warmed at 37° C. for 30 min.

Then, the phenol extraction was performed by adding 0.5% bentonite suspension (50 $\mu$l) and TE-saturated phenol (150 $\mu$l) to the above mixture followed by the second extraction using a mixture of phenol:chloroform (1:1, v/v). The aqueous layer was extracted with chloroform. To this aqueous layer were added 3M sodium acetate (10 $\mu$l) and cold ethanol (250 $\mu$l), and the mixture was left to stand at −80° C. for 30 min. Then the mixture was centrifuged at 15,000×g for 5 min to obtain precipitates. The precipitates were washed by centrifugation in 70% ethanol. After removing the ethanol by drying, the precipitates thus obtained were dissolved in distilled water (50 μl). To this solution was added 4M lithium chloride (50 μl), and the resulting mixture was left to at stand ice-cold overnight.

Then the above mixture was centrifuged at 15,000×g for 5 min to obtain precipitates, which were washed again by centrifugation in 70% ethanol as above. After the removal of ethanol by drying, the precipitates were dissolved in distilled water (8 μl) and stored as the RNA sample.

EXAMPLE 3 cDNA Cloning cDNA was prepared from the RNA sample prepared in Example 2 using a cDNA synthesis kit (Amersham) according to the protocol specified by the supplier, and dissolved in TE buffer (1 μl).

Then, plasmid pU119 (500 ng/μl) was digested with SmaI and then dephosphorylated. To the digest (2 μl) were added the synthesized cDNA (1 μl), 10 mM ATP, 10×ligation buffer (Behringer), T4DNA ligase (5 U/μl, Behringer) and distilled water (13 μl), and the mixture was incubated at 22° C. overnight for ligation.

Competent cells of *Escherichia coli* MV1184 were prepared, and mixed with the ligation reaction solution (100 μl), being left to stand on ice for 30 min.

Then, the reaction solution was warmed at 37° C. for 60 sec, immediately ice-cooled, mixed with SOC medium (500 μl), and the resulting mixture was kept at 37° C. for 1 hr. To this mixture were added 50 μl each of 2% X-gal and 100 mM IPTG, and the resulting mixture was spread over two 2×YT agar plates containing ampicillin (50 μg/ml), and incubated at 37° C. overnight.

From white colonies of E. coli thus obtained were extracted plasmid DNAs by standard methods, and cells having long cDNA fragments inserted were selected and stored.

Then, to confirm cDNAs to be derived from the HLV genome, purified HLV-RNA sample was partially denatured in alkali, and selected single-stranded cDNAs were subjected to Southern hybridization using a probe labeled at the 5'-terminus with [γ$^{32}$P]ATP by T4 polynucleotide kinase.

As a result, E. coli strains harboring plasmid with cDNA insert fragments 0.7 kb, 1.2 kb, 1.35 kb, 3.5 kb and 5.0 kb long derived from the HLV genome were obtained.

EXAMPLE 4

Determination of the Base Sequence of cDNA Derived from the HLV Genome

E. coli cells harboring plasmid with cDNA insert fragments derived from the HLV genome obtained in Example 3 were shake-cultured in 2×YT medium at 37° C. overnight, and plasmid were purified by standard methods. cDNA fragments derived from the HLV genome were prepared from the plasmid by standard methods, and, with the fragments as a template, they were decoded for their base sequence by the dideoxy method (Sanger et al., Proc. Natl. Acad. Sci., 74, 5463 (1977)) using a DNA sequencer (ABI) and a sequence kit (USB, SEQUENASE) to determine the sequence 1375 base long thereof.

As a result, the translation region (base sequence from 58th to 975th of the sequence identification number 1 in the sequence listing) putatively coding for the HLV coat protein gene (encoding 306 amino acid residues; molecular weight about 31.4 kD) and that (molecular weight about 12.0 kD, base sequence from 981st to 1292nd of the sequence identification number 1 in the sequence listing) encoding the protein (101 amino acid residues) were identified.

In addition, putative amino acid sequences translated from each base sequence are shown in the sequence identification numbers 6 and 7 in the sequence listing. Among them, since the amino acid sequence shown in the sequence identification number 6 comprises the sequence corresponding to a partial amino acid sequence of the HLV coat protein described in detail below, its presence was confirmed.

This invention is highly expected to contribute to the production of hop resistant to said virus by transforming the gene encoding HLV coat protein thus obtained. Therefore, the transformation of microbes such as Escherichia coli, etc. with said coat protein encoding gene thus obtained enables the production of said protein. Also, based on the amino acid sequence of said protein, any fragments thereof can be obtained using, for example, a protein synthesizer, etc. The coat protein or fragments thereof can be used for the production of HLV antibodies usable for the detection of HLV.

EXAMPLE 5

Determination of the Partial Amino Acid Sequence of the HLV Coat Protein

The purified HLV protein sample (1 μg/μl, 120 μl) prepared in Example 1 was partially digested with a proteolytic enzyme (Lysyl Endopeptidase, Wako Pure Chemicals) at room temperature (25 ° C.) for 16 hrs. Peptide fragments thus obtained were purified by fractionation by reversed phase HPLC (using RepRPC HR5/5 column, Pharmacia), and analyzed for their amino acid sequence of the N-terminus with a protein sequencer (ABI). Amino acid sequence at the N terminus of three peptide fragments were found to be completely identical to the putative amino acid sequence of the HLV coat protein. The N-terminus amino acid sequence of these three peptide fragments and their locations in the amino acid sequence of the HLV coat protein are shown in FIG. 1.

EXAMPLE 6

Gene diagnosis of virus by the reverse transcription PCR of the HLV-infected hop Leaves of the HLV-infected hop (cultivar, Shinshu Wase) and virus-free hop (cultivar, Shinshu Wase) (0.1 g each) were ground in 0.05M phosphate buffer (pH 8.0, 1 ml) and extracted with chloroform. After the supernatant was treated with phenol and then with ether three times, ethanol was added thereto to precipitate nucleic acids. The precipitates thus obtained were washed by centrifugation in 70% ethanol, and, after the excess ethanol was removed by drying, dissolved in TE buffer (100 μl). A 2 μl aliquot thereof was subjected to the reverse transcription PCR.

Four different primers for PCR were designed based on the present base sequence and synthesized by standard methods using a DNA synthesizer Model 380B (ABI), having the base sequences described in the sequence identification numbers from 2 to 5 (designated 3P, 4P, 3M and 4M, respectively). Each primer was used in combinations of 3P/3M, 4P/3M, 3P/4M and 3P/4M for the reverse transcription PCR.

The reverse transcription reaction was performed in Tris-HCl buffer (pH 8.3) consisting of 75 mM KCl, 3 mM $MgCl_2$, 10 mM DTT and 0.5 mM dNTPs with the complementary strand primer (25 pmol), a reverse transcriptase (ANV-RTase XL, Takara Shuzo, 5 units) and the hop nucleic acid prepared above (2 μg) added thereto at 55° C. for 30 min.

Then, to the above reaction mixture were added a thermostable DNA polymerase (Behringer, 0.5 unit) and the primer for amplification (25 pmol), and the PCR was performed. The volume of the reaction solution was made up to 10 μl, and mineral oil (20 l) was layered on top to prevent the evaporation of the reaction mixture.

Each step in PCR was performed under the following conditions. One PCR cycle consisted of the denaturation step at 94° C. for 1 min, the primer annealing step at 55° C. for 1 min and the DNA elongation step at 72° C. for 2 min. After 30 cycles of PCR, the reaction solution was kept at 72° C. for 5 min, and stored at 4° C.

The amplified genomic DNAs obtained by PCR described above were analyzed by agarose gel electrophoresis.

The DNAs were fractionated by electrophoresis on 2% agarose gel in Tris-borate buffer (pH 8.0) containing 2 mM EDTA at 100 V for 30 min. DNA molecular weight markers, λDNA digests by restriction enzymes HindIII and EcoRI (Nippon Energy) were used as the size marker.

After the completion of electrophoresis, gel was immersed in an aqueous solution of ethidium bromide (0.5 μg/ml) for 10 min, and then irradiated with UV 254 nm in the dark to detect red bands of DNA-ethidium bromide complex.

Figure 2:
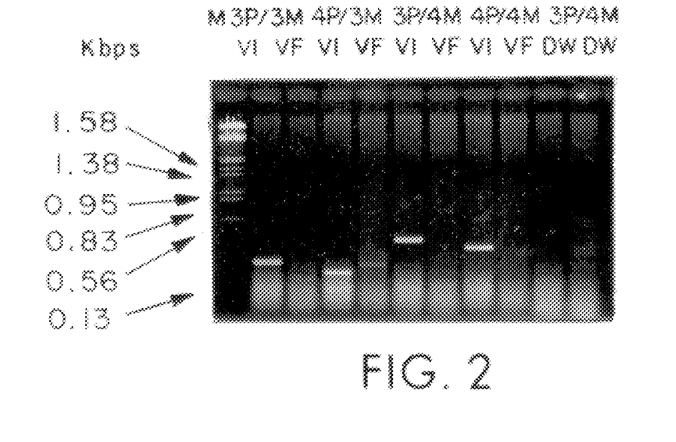
FIG. 2 shows an electrophoretic photograph depicting results of the gene diagnosis of the hop latent virus using PCR.

Results of electrophoresis (repeated twice) are shown in FIG. 2, wherein DW stands for sterilized water.

As the result of agarose gel electrophoresis, specific DNA amplified fragments were obtained from the HLV-infected hop depending on the primers used, but were not obtained from the uninfected hop, enabling us to distinguish between the two.

The specific DNA amplified fragments corresponding to the primers used were as follows, 3P/4M: 233 base pairs, 4P/3M: 181 base pairs, 3P/4M: 377 base pairs and 4P/4M: 325 base pairs.

EXAMPLE 7

Gene diagnosis by Dot Blot Hybridization

Leaves from the HLV-infected hop (cultivar: Shinshu Wase) and the virus-free hop (cultivar: Shinshu Wase) (0.1 g each) were ground in 0.05M phosphate buffer (pH 8.0, 1 ml) and extracted with chloroform. After the supernatant was treated with chloroform and then with ether three times, ethanol was added thereto to precipitate nucleic acids. Then, the precipitates thus obtained were washed by centrifugation in 70% ethanol, and dissolved in TE buffer (100 μl) after the excess of ethanol had been evaporated. A 2 μl-aliquot thereof was added to three volumes of the nucleic acid denaturing buffer (consisting of 65% formamide, 20% formaldehyde, 1.54M MOPS, 6.5 mM sodium acetate and 1.3 mM EDTA), and the mixture was heated at 65° C. for 15 min and then immediately cooled. To this solution was added 8 μl of 20×SSC (consisting of 0.15M sodium chloride and 0.015M sodium citrate at pH 7.0), and mixed. A 10 l-aliquot thereof was dropped on a membrane filter (Amersham, trade name Hybond-N+) and subjected to dot blot hybridization.

As the result of elucidation of the gene structure coding for the HLV coat protein and development of the gene diagnosis of HLV in the present invention, tedious procedures such as the conventional isolation of HLV, preparation of antiserum, purification of antibody, etc. become unnecessary and the virus diagnosis of the HLV-infected hop which is more convenient and accurate than ELISA becomes available. Furthermore, the present invention may contribute to the production of a hop resistant to HLV by the utilization of this virus.

---

What is claimed is:

1. An isolated DNA molecule encoding a coat protein of hop latent virus, wherein said DNA molecule consists of SEQ ID NO:1 or a sequence fully complementary thereto.

2. An isolated DNA molecule encoding 306 amino acid residues of SEQ ID NO:6.

3. An isolated DNA molecule encoding 104 amino acid residues of SEQ ID NO:7.

4. An isolated DNA molecule consisting of 18 to 1375 contiguous nucleotides of SEQ ID NO:1, wherein said DNA molecule detects hop latent virus.

5. The isolated DNA molecule of claim 4 comprising SEQ ID NO:2.

6. The isolated DNA molecule of claim 4 comprising SEQ ID NO:3.

7. The isolated DNA molecule of claim 4 comprising SEQ ID NO:4.

8. The isolated DNA molecule of claim 4 comprising SEQ ID NO:5.

9. A method for detecting hop latent virus, wherein said method comprises:
  amplifying DNA in a sample of nucleic acid isolated from hop, wherein said amplification is performed using reverse transcription polymerase chain reaction using the isolated DNA according to any one of claims 4–8 as primers;
  electrophoretically analyzing the amplified products thus obtained; and
  correlating the presence of amplified DNA of a specific length to presence of the hop latent virus.

10. A method for detecting hop latent virus, wherein said method comprises:
  amplifying DNA in a sample of nucleic acid isolated from hop, wherein said amplification is performed using reverse transcription polymerase chain reaction using the isolated DNA of SEQ ID NO:2 and SEQ ID NO:4 as primers;
  electrophoretically analyzing the amplified products thus obtained; and
  correlating the presence of amplified DNA of 233 base pairs to presence of the hop latent virus.

11. A method for detecting hop latent virus, wherein said method comprises:
  amplifying DNA in a sample of nucleic acid isolated from hop, wherein said amplification is performed using reverse transcription polymerase chain reaction using the isolated DNA of SEQ ID NO:3 and SEQ ID NO:4 as primers;
  electrophoretically analyzing the amplified products thus obtained; and
  correlating the presence of amplified DNA of 181 base pairs to presence of the hop latent virus.

12. A method for detecting hop latent virus, wherein said method comprises:
  amplifying DNA in a sample of nucleic acid isolated from hop, wherein said amplification is performed using reverse transcription polymerase chain reaction using the isolated DNA of SEQ ID NO:2 and SEQ ID NO:5 as primers;

electrophoretically analyzing the amplified products thus obtained; and correlating the presence of amplified DNA of 377 base pairs to presence of the hop latent virus.

13. A method for detecting hop latent virus, wherein said method comprises:

amplifying DNA in a sample of nucleic acid isolated from hop, wherein said amplification is performed using reverse transcription polymerase chain reaction using the isolated DNA of SEQ ID NO:3 and SEQ ID NO:5 as primers;

electrophoretically analyzing the amplified products thus obtained; and correlating the presence of amplified DNA of 325 base pairs to presence of the hop latent virus.

14. A method for detecting hop latent virus, wherein said method comprises:

hybridizing nucleic acid isolated from hop with isolated DNA identified by SEQ ID NOS:4 and 5 or DNA complementary thereto; and correlating the presence of hybridized nucleic acid with the presence of hop latent virus.

15. A method for detecting hop latent virus, wherein said method comprises:

hybridizing nucleic acid isolated from hop with restriction enzyme fragments of SEQ ID NO:1 as a probe; and correlating the binding of said probe with said nucleic acid to the presence of hop latent virus.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1375 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO:1:

```
TAAAGTGTTG  CAAATAGTGT  AGCTTTAGGT  GTTTAGCAGT  AGATCGAAGT  TGAAGCAATG      60

GCCGACAAAC  AAGGACAGAT  GACTGAACAA  CAGAAGGTGG  ATTCTCAGAA  GCTGCAGGGG     120

GAAGCAAAGA  ATAAAGAAAA  AGCTGAGTCC  TCAAAGAGGA  AAGATGAGTT  GCTTAAGAAG     180

TACATTGATC  CTGGGCTAGG  GTCTGATGAT  GATGAAGAGG  AGATGGTGGA  ATTGAGATTG     240

AGCAAATTGA  GGGAGTTCCT  GGCTCGTAGA  AGGGCCGCTA  TTCGCGTGAC  TAACGCAGGG     300

CTAGAAACAG  GCAGGCCCGC  ACTCAAGCCC  ACACCCGACA  TGCTGCCTGA  CCCTACCAAC     360
```

```
CCGTACAATA  AACCCTCGTT  GGATGCTTTG  TTGATGATTA  AGCCTAGGGT  CGTGTCAAAC       420

AACATGGCCA  CCTCAGAGGA  TATGATGAAG  ATCTGCGTTG  ATCTGGAGGG  GTTGGGCGTG       480

CCCACTGAAC  ACGTGCAAAG  CGTGATCTTG  CAAGCGGTGT  TCTATTGCAA  GGACTCCAGC       540

AGTTCACCCT  ATGTGGACCC  TCGGGGCTCT  TTCGAGTGGC  GTGGTGGGGC  GATCTCGGCC       600

GATTCAGTGC  TTGCGATAAT  AAAGAAGGAT  GCCGAGACCT  TGAGGCGCGT  CTGCAGGTTG       660

TATGCACCAC  TCACGTGGAA  CTACATGTTG  CTACATAACA  ATCCCCTTC   TGACTGGTCC       720

GAAATGGGCT  TTCAGCGCGA  AGATCGCTTT  GCTGCTTTTG  ATTGCTTGGA  TTACGTTGAA       780

AATGCTGCGG  CTGTGCAACC  ATTGGAAGGG  CTGATCAGAG  TCCCCACAGC  AAGAGAGAAG       840

ATTGCAAATA  AGACTCATAA  GGATCTAGCG  CTGCGCCGTG  CGAATAGGAA  TCAGCTTTTC       900

GGGAATCTGG  ATGTGGAAAT  AACCGGGGGA  AAGAATGGGC  CCGAGCTTCA  ACGCGACTAC       960

TCTAAGTCTA  ATAATTGAGT  ATGTTTACC   TGCGTGTCGC  TTTGCTGTTG  CATAATAAGT      1020

TCTTAGAACA  GTGTGGTAGG  AGTGATTTTC  ATTTGTGTGT  TATGATTTCT  CTGCAAGTCC      1080

ATCGCCCTGT  GGGGGTTGGA  AGGTCGTCGT  ATGCTAGAAG  GCGTAGAGCT  AAGCTAGTAG      1140

GTCGCTGCCA  CCGGTGTTAC  CGGTTGTGGC  CACCTACGGC  TTTCACTACG  AGGTGTGATA      1200

ATAAACATG   CTTTCCTGGC  CTAACTTACA  ATGCTAGCAT  TGCTAGGTTC  ATACGAGATG      1260

GAGTAACTGA  GGTGATACCA  TCTGCACCCA  ACTAGTGTGG  GGGTGGCCGC  TAAAGCCTAT      1320

TTAATATATA  AGGCGTGTCA  CTATAATAAA  ACTTTGGTTT  TTAAATATTT  TCACC           1375
```

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: other nucleic acid     ( x i ) SEQUENCE DESCRIPTION: SEQ ID NO:2:

```
TAGGGTCGTG  TCAAACAAC                                                         19
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: other nucleic acid     ( x i ) SEQUENCE DESCRIPTION: SEQ ID NO:3:

```
GTTGATCTGG  AGGGGTTG                                                          18
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: other nucleic acid     ( x i ) SEQUENCE DESCRIPTION: SEQ ID NO:4:

```
TCTCGGCATC  CTTCTTTATT                                                        20
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: other nucleic acid     ( x i ) SEQUENCE DESCRIPTION: SEQ ID NO:5:

TTTCAAGTAA TCCAAGCAAT                                          20

( 2 ) INFORMATION FOR SEQ ID NO:6:

( i ) SEQUENCE CHARACTERISTICS:
        ( A ) LENGTH: 306 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:6:

```
Met Ala Asp Lys Gln Gly Gln Met Thr Glu Gln Gln Lys Val Asp Ser
 1               5                  10                  15

Gln Lys Leu Gln Gly Glu Ala Lys Asn Lys Glu Lys Ala Glu Ser Ser
            20                  25                  30

Lys Arg Lys Asp Glu Leu Leu Lys Lys Tyr Ile Asp Pro Gly Leu Gly
        35                  40                  45

Ser Asp Asp Asp Glu Glu Glu Met Val Glu Leu Arg Leu Ser Lys Leu
    50                  55                  60

Arg Glu Phe Leu Ala Arg Arg Ala Ala Ile Arg Val Thr Asn Ala
65                  70                  75                  80

Gly Leu Glu Thr Gly Arg Pro Ala Leu Lys Pro Thr Pro Asp Met Leu
                85                  90                  95

Pro Asp Pro Thr Asn Pro Tyr Asn Lys Pro Ser Leu Asp Ala Leu Leu
               100                 105                 110

Met Ile Lys Pro Arg Val Val Ser Asn Asn Met Ala Thr Ser Glu Asp
           115                 120                 125

Met Met Lys Ile Cys Val Asp Leu Glu Gly Leu Gly Val Pro Thr Glu
       130                 135                 140

His Val Gln Ser Val Ile Leu Gln Ala Val Phe Tyr Cys Lys Asp Ser
145                 150                 155                 160

Ser Ser Ser Pro Tyr Val Asp Pro Arg Gly Ser Phe Glu Trp Arg Gly
               165                 170                 175

Gly Ala Ile Ser Ala Asp Ser Val Leu Ala Ile Ile Lys Lys Asp Ala
           180                 185                 190

Glu Thr Leu Arg Arg Val Cys Arg Leu Tyr Ala Pro Leu Thr Trp Asn
       195                 200                 205

Tyr Met Leu Leu His Asn Asn Pro Pro Ser Asp Trp Ser Glu Met Gly
   210                 215                 220

Phe Gln Arg Glu Asp Arg Phe Ala Ala Phe Asp Cys Leu Asp Tyr Val
225                 230                 235                 240

Glu Asn Ala Ala Ala Val Gln Pro Leu Glu Gly Leu Ile Arg Val Pro
               245                 250                 255

Tyr Ala Arg Glu Lys Ile Ala Asn Lys Thr His Lys Asp Leu Ala Leu
           260                 265                 270

Arg Arg Ala Asn Arg Asn Gln Leu Phe Gly Asn Leu Asp Val Glu Ile
```

-continued

```
                    275                   280                          285
        Thr Gly Gly Lys Asn Gly Pro Glu Leu Gln Arg Asp Tyr Ser Lys Ser
            290                 295               300

Asn Asn
        305
```

( 2 ) INFORMATION FOR SEQ ID NO:7:

( i ) SEQUENCE CHARACTERISTICS:
    ( A ) LENGTH: 104 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

```
Met Phe Tyr Leu Arg Val Ala Leu Leu Leu His Asn Lys Phe Leu Glu
1               5                   10                  15

Gln Cys Gly Arg Ser Asp Phe His Leu Cys Val Met Ile Ser Leu Gln
            20                  25                  30

Val His Arg Pro Val Gly Val Gly Arg Ser Ser Tyr Ala Arg Arg Arg
        35                  40                  45

Arg Ala Lys Leu Val Gly Arg Cys His Arg Cys Tyr Arg Leu Trp Pro
    50                  55                  60

Pro Thr Ala Phe Thr Thr Arg Cys Asp Asn Lys Thr Cys Phe Pro Gly
65              70                  75                  80

Leu Thr Tyr Asn Ala Ser Ile Ala Arg Phe Ile Arg Asp Gly Val Thr
            85                  90                  95

Glu Val Ile Pro Ser Ala Pro Asn
            100
```